US008593515B2

(12) United States Patent
Detrois et al.

(10) Patent No.: US 8,593,515 B2
(45) Date of Patent: Nov. 26, 2013

(54) METHOD FOR QUALITY CONTROL OF PLASTIC CONTAINERS

(75) Inventors: Christian Detrois, Golbey (FR); Peter Lindner, Langquaid (DE); Rainer Kwirandt, Barbing (DE); Anton Niedermeier, Offenstetten (DE); Stefan Piana, Köfering (DE)

(73) Assignee: Krones AG, Neutraubling (DE)

( * ) Notice: Subject to any disclaimer, the term of this patent is extended or adjusted under 35 U.S.C. 154(b) by 1196 days.

(21) Appl. No.: 12/066,883

(22) PCT Filed: Aug. 29, 2006

(86) PCT No.: PCT/EP2006/008448
§ 371 (c)(1),
(2), (4) Date: Jul. 17, 2008

(87) PCT Pub. No.: WO2007/031194
PCT Pub. Date: Mar. 22, 2007

(65) Prior Publication Data
US 2009/0147082 A1  Jun. 11, 2009

(30) Foreign Application Priority Data

Sep. 15, 2005 (DE) .......................... 10 2005 044 206

(51) Int. Cl.
*G01N 21/00* (2006.01)
*H04N 9/47* (2006.01)
(52) U.S. Cl.
USPC .......................... 348/127; 348/92; 356/239.4
(58) Field of Classification Search
USPC ................. 256/239.4; 348/92, 127; 356/239.4
See application file for complete search history.

(56) References Cited

U.S. PATENT DOCUMENTS

| 5,591,462 | A  | * | 1/1997  | Darling et al. | 425/173   |
|-----------|----|---|---------|----------------|-----------|
| 6,239,870 | B1 | * | 5/2001  | Heuft          | 356/239.5 |
| 6,473,169 | B1 | * | 10/2002 | Dawley et al.  | 356/239.4 |
| 6,650,405 | B2 | * | 11/2003 | Lam et al.     | 356/33    |
| 6,975,410 | B1 | * | 12/2005 | Sturgill       | 356/631   |

FOREIGN PATENT DOCUMENTS

| DE | 197 41 384 A1 | 3/1999 |
| DE | 69522028 T2 | 11/2001 |
| JP | 09269299 A | 10/1997 |
| JP | 2001517792 A | 10/2001 |
| JP | 2002513463 A | 5/2002 |
| WO | WO 97/46429 | 12/1997 |

OTHER PUBLICATIONS

Office Action from parallel Japanese application P2008-530366, dated Sep. 20, 2011.
PCT International Preliminary Report on Patentability and Written Opinion of the International Searching Authority based on International Patent Application No. PCT/EP2006/008448; International Filing Date: Aug. 29, 2006; Date of Issuance of Report: Apr. 8, 2008.
German Office Action for 102005044206.4, dated Feb. 27, 2013.

\* cited by examiner

*Primary Examiner* — Aaron Strange
(74) *Attorney, Agent, or Firm* — Marshall, Gerstein & Borun LLP

(57) ABSTRACT

A method for quality control of a stretch-blow-molded plastic container by inspecting its base, which method is easy to execute and is not highly susceptible to faults. Such inspection of the container bases includes determining quality features such as the surface area of an unstretched and/or only slightly stretched region of the base of the plastic container.

20 Claims, 3 Drawing Sheets

METHOD FOR QUALITY CONTROL OF PLASTIC CONTAINERS

The present application claims the benefit of priority of International Patent Application No. PCT/EP2006/008448, filed on Aug. 29, 2006, which application claims priority of German Patent Application No. 10 2005 044 206.4, filed Sep. 15, 2005. The entire text of the priority application is incorporated herein by reference in its entirety.

FIELD OF THE DISCLOSURE

The present disclosure relates to a method for controlling the quality of a stretch-blow-molded plastic container and, preferably, for monitoring and controlling the stretch-blow-molding process.

BACKGROUND

A method for quality control is known from U.S. Pat. No. 6,872,895. The known method determines the conditions at the base of a stretch-blow-molded plastic container as indication for a successfully and correctly executed stretch-blow-molding process. However, this known method only determines the mass or volume of the material in the base of the plastic container. To this end, the absorption characteristics of the whole base or of a selected area of said base are determined and, on the basis of this determination, conclusions are drawn with regard to the mass or the volume of the material which still exists in the base after the stretch-blow-molding process. The features taken into account in the absorption measurement comprise, however, also features, such as minor cloudiness or the like, which do not have any influence on the quality of the plastic container and which may corrupt the measurement. Meaningful absorption measurements are, moreover, comparatively complicated. An area-integrating absorption measurement with a non-spatially-resolving sensor is not very meaningful because of the non-linear characteristics of the law of absorption, and, when a spatially-resolving sensor is used, such measurements are extremely complicated, especially in the infrared light region.

Furthermore, it is known e.g. from DE 199 14 028 to determine the quality of a stretch-blow-molded plastic container in that the outer contours of various areas of the container and the ratio of said contours to one another are determined in a transmitted light process. This method does, however, not allow a reliable detection of all deviations.

Furthermore, a great variety of wall thickness determination methods of stretch-blow-molded plastic containers is known, one of said methods being known e.g. from DE-A-101 16 665. A wall thickness measurement must, however, be executed at many different points of the plastic container so as to be meaningful for the quality of the container in its entirety. The method described in this publication can be used for determining, analogously to the wall thickness, also other parameters, such as the density. The known method is therefore comparatively complex.

SUMMARY OF THE DISCLOSURE

It is therefore the object of the present disclosure to provide a method for controlling the quality of a stretch-blow-molded plastic container as well as for monitoring and controlling the stretch-blow-molding process, which method is easy to execute and largely insusceptible to faults.

The disclosure is based on the finding that, depending on the respective process control, the stretching of the base of a plastic container leads to different characteristic distributions of material in said base. These inhomogenities can be emphasized by special illumination according to the present disclosure and can be recorded in a spatially resolved manner with electronic camera technology, especially also in visible light. Making use of image processing algorithms according to the present disclosure, the characteristic distributions of material are measured and used for determining therefrom characteristic reference numbers, such as the surface area of an unstretched and/or only slightly stretched region of the base of the plastic container and/or the size and the position of the transition area between the unstretched and the stretched region. A parameter which is very meaningful for the quality of the stretch-blow-molding process and for the quality of the stretch-blow-molded plastic container can easily be provided in this way. The thus obtained information content is much higher than in the case of conventional methods, such as the determination of the section weight or of the wall thickness at individual points of the side wall.

The characteristic distributions of material can be made visible with various methods, e.g. the wedge angle between the inner and the outer wall by means of directed light, material stresses with the aid of polarized light, or, in the case of deep-dyed container materials, also with the aid of absorption in the visible wavelength region. A combination of illuminations which are more or less strongly directed, illuminations with different wavelengths in the visible or infrared or ultraviolet wavelength region, or illuminations having different directions of polarization are imaginable as well.

Depending on what is easier to realize, this method can be applied to the whole container base or to subareas thereof.

The determination in the transmitted light process is specially preferred and is particularly suitable for light-transmissive PET plastic bottles.

The characteristic reference numbers determined in the process are preferably used for controlling the stretch-blow-molding process by means of process parameter control.

Since the method simultaneously represents an online quality control of all the containers produced, and since the product quality also depends on multiply provided production tools, such as the cavities of the stretch-blow-molding machine, the container quality measured is preferably statistically associated with the respective production tools.

BRIEF DESCRIPTION OF THE DRAWINGS

In the following, embodiments of the present disclosure will be explained in detail on the basis of the drawings, in which.

DETAILED DESCRIPTION OF THE PREFERRED EMBODIMENT

Figure 1:
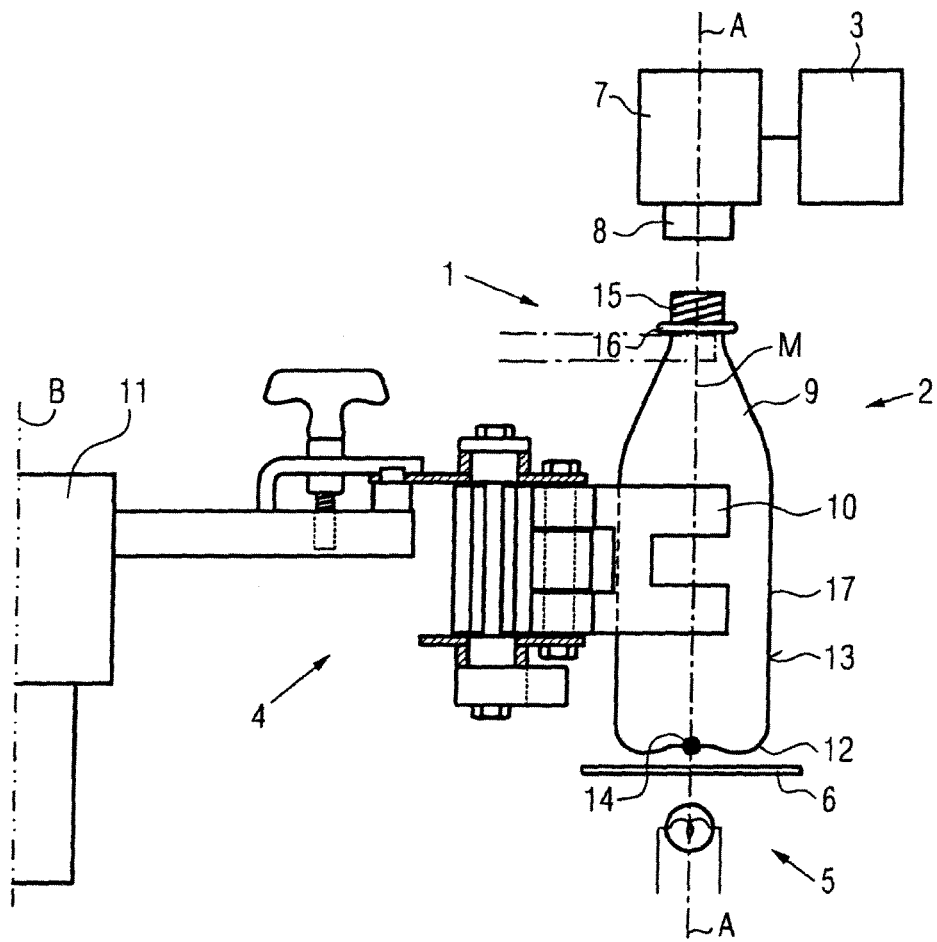
FIG. 1 shows a schematic representation of a quality control apparatus for use in the method according to the present invention.

FIG. 1 shows an embodiment of an apparatus 1 for executing the method according to the present disclosure. The apparatus comprises a control station 2, an evaluation means 3 and a transport unit 4. A plastic container to be inspected 9—the container shown in FIG. 1 is a plastic bottle consisting preferably of PET—is held through the transport unit 4 by a clamp element 10 such that its base and its mouth are free.

The container 9 has a shape that is substantially rotationally symmetric with regard to a longitudinal axis M. The wall 13 of the container 9 comprises a mouth region 15, which is provided with an external thread and a laterally projecting support ring 16, and a substantially cylindrical body area 17, which is located below the support ring 16 and which laterally projects beyond said support ring 16, said body area 17 defining the largest outer diameter of the container 9. The body area 17 terminates in a base 12, which is implemented as a foot. On the outer side of the base 12, an injection point 14 is provided.

The transport star wheel 11 having the axis of rotation B comprises a plurality of the transport units 4 shown. The transport star wheel 11 is arranged after, preferably immediately after a conventional stretch-blow-molding machine, which is not shown in the drawing and which is used for producing the plastic containers 9, but it may also be provided at some other location. However, it should preferably be possible to precisely associate each container 9 to stations of its production. In this stretch-blow-molding machine, preforms are subjected to blowing so as to establish their desired final shape; in so doing, said preform is stretched and enlarged while reducing its wall thickness.

The transport star wheel 11 conducts the molded and stretched plastic containers 9 through the control station 2 for the purpose of quality control.

The control station 2 is implemented as a transmitted-light examination unit and comprises a stationary light source 5, preferably an optical unit 6, a sensor 7, preferably a camera (matrix camera) and an imaging objective 8. The optical axis A of the optical components of the control station 2 is arranged in such a way that it coincides with the centre line M of a correctly shaped plastic container 9, when said container 9 is being transported through the control station 2. The light source 5 with the optical components which are preferably associated with said light source 5 are located below the base 12 of the container 9, whereas the sensor 7 and the components associated therewith are arranged on the side of the mouth 15 of the container 9 and are directed into the mouth opening. The sensor 7 is connected to the evaluation means 3.

The optical unit 6 can comprise e.g. a stop, a directing foil and/or a lens system or other optical units which are able to generate directed, in particular strongly directed, so-called hard light.

Figure 4:
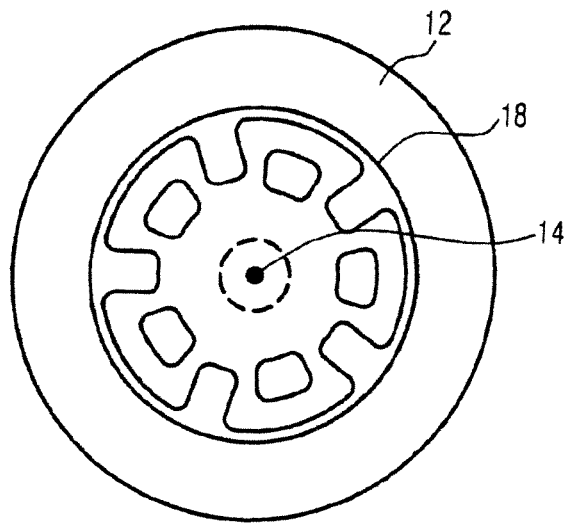
FIG. 4 shows a photographic representation of a surface area determined according to a further embodiment.
Figure 5:
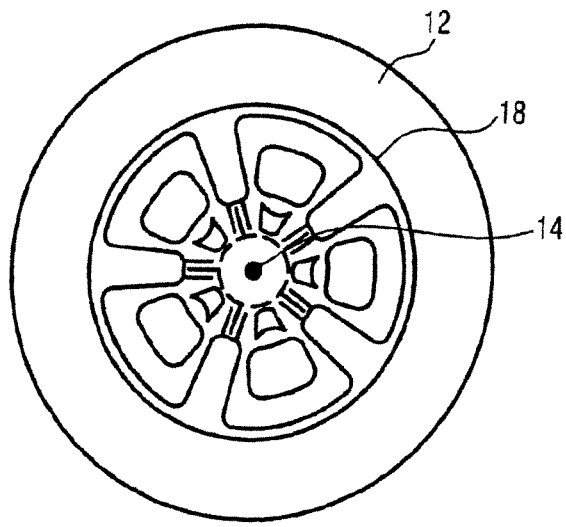
FIG. 5 shows a photographic representation of a surface area determined according to a further embodiment.

If such directed light is directed onto the base 12, in particular in the area of the center line M, where the injection point 14 is located, a dark outer contour of the type shown in detail in FIGS. 4 and 5 will appear around the injection point 14. All the parts of the container base in the case of which the inner and the outer wall are not plane parallel, but define a wedge angle, whereby the directed light is deflected by diffraction and does not arrive at the camera, are imaged darkly. The image according to FIG. 4 is obtained when strongly directed light is used, whereas the image according to FIG. 5 is obtained, when less strongly directed light is used, in which case the outer contour 18 and the dark spot in the middle appear brighter so that further details can still be seen.

It turned out that the surface area within the dark outer contour 18 is a measure for the quality of the stretch-blow-molding process, since the dark outer contour 18 encloses an unstretched and/or only slightly stretched region, the size of this region being a measure for the quality of the stretch-blow-molding process. Hence, a reference value for the surface area of region 18, which indicates a container 9 of satisfactory quality, was ascertained. This reference value indicates that, on the one hand, the region 18 is not excessively large, i.e. the base 12 does not comprise an excessive amount of unstretched material which would then be missing at other locations, e.g. in particularly sensitive areas of the wall, and that, on the other hand, the base 12 does not comprise an excessively small amount of unstretched or only slightly stretched material, which may be a sign of irregular heating and of an increased wall thickness at some other point.

Figure 2:
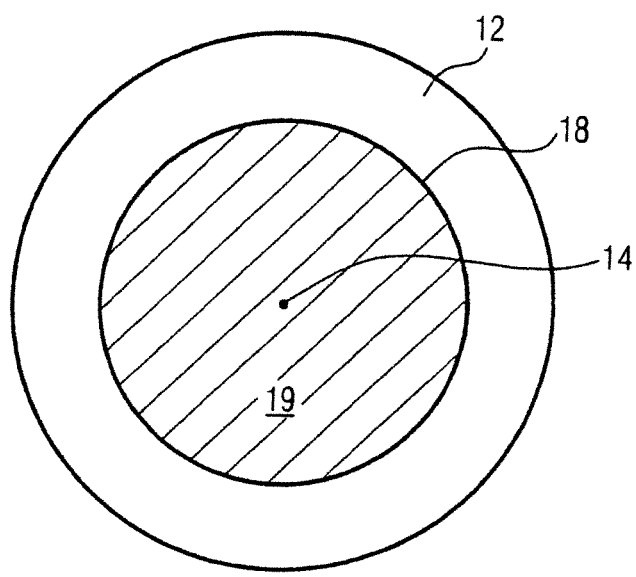
FIG. 2 shows a schematic representation of a surface area determined according to a first embodiment.

For quality control, the surface area of said region 18 is determined, as shown in FIG. 2, either in that the total size 19 of the whole area enclosed by the shaded region 18 is determined.

Figure 3:
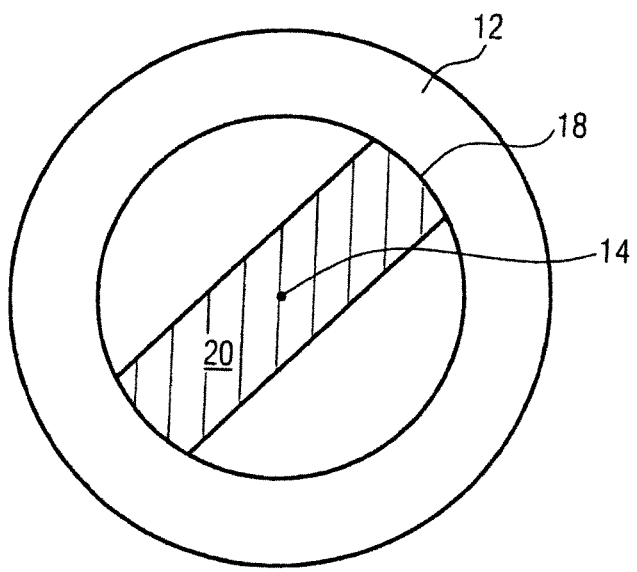
FIG. 3 shows a schematic representation of a surface area determined according to a further embodiment.

Furthermore, it is also possible to determine the surface area of the unstretched region by determining only the surface area of a subregion 20 and by extrapolating from this subregion 20 to the total surface area. The subregion 20 is preferably measured at a representative, meaningful location; in FIG. 3, a subregion 20 is shown, which extends in the form of a strip, symmetrically with regard to the center line M and the injection point 14, across the whole unstretched region 18.

Additional quality features can be determined from the darkly imaged transition region between the unstretched or only slightly stretched region in the middle of the base and the stretched region at the periphery of the base. Features which are meaningful as regards the quality of the stretch-blow-molding process are the width, the position, the shape and the degree of shading of this region.

The optical unit 6 may, however, also be implemented as a polarizer for generating polarized light. By means of the polarized light, material stresses in the base 12 can be made visible so that it is possible to extrapolate from the presence and absence of material stresses in the various regions of the base 12 to the size of the unstretched and/or only slightly stretched region 18.

The quality features determined or received from the sensor 7 are supplied to the evaluation means 3. The evaluation means 3 compares the quality features with the reference value and determines whether the plastic container 9 measured satisfies the demands on quality or whether it must be rejected. It will be expedient when the reference value has the form of a tolerance range between upper and lower threshold values.

If it has been determined that a plastic container 9 does not satisfy the demands on quality, the evaluation means 3 will also be able to intervene in the production process of the plastic container 9 and to control process parameters by way of example. Such process parameters can e.g. be the heating temperature in the individual heating zones.

As modification of the embodiments described hereinbefore and shown in the drawings, the control station can be arranged at any other suitable location. The transport unit can have any structural design which allows the base to be inspected in a transmitted light process, e.g. it may also be a chainlike transport unit, or a transport unit which holds the containers below the mouth or the support ring (indicated by a dot and dash line in FIG. 1).

The invention claimed is:

1. A method for controlling the quality of a stretch-blow-molded plastic container (9), the method comprising optically inspecting a container base (12) of the plastic container, making visible one or both of (a) characteristic structures of the container base and (b) distribution of material (18, 19, 20) at the container base (12) of the plastic container (9) by illumination means, recording the characteristic structures and distribution of material with at least one camera, deriving quality features therefrom by image processing algorithms, and making visible one or both of the characteristic structures and the distribution of material through a recognition of a wedge angle between inner and outer surfaces of the container with the aid of directed light, whereby the directed light at the wedge angle does not arrive at the camera.

2. A method according to claim 1, and making visible one of or both the characteristic structures and the distribution of material through a recognition of material stresses with the aid of polarized light.

3. A method according to claim 1, and making visible one of or both the characteristic structures and the distribution of material through a recognition of the absorption of visible light by deep-dyed plastic material.

4. A method according to claim 1, and making visible one of or both the characteristic structures and the distribution of material through a recognition of patterns.

5. A method according to claim 4, wherein the recognition of patterns are one of applied to or in the illumination means and which become visible through the container base in a distorted fashion.

6. A method according to claim 1, and via the illumination means illuminating the container base, and via the electronic camera viewing the base through the container mouth opening in a transmitted light process.

7. A method according to claim 1, and comparing individual quality features or a combination of such features with predefined limits, and, if the limit values are exceeded, removing the containers objected to.

8. A method according to claim 1, and statistically associating the determined quality features and the derived magnitudes, respectively, with the respective multiply provided production tools in the stretch-blow-molding machine.

9. A method according to claim 1, further comprising controlling the parameters of the stretch-blow-molding process in response to at least one of the desired quality features.

10. A method according to claim 1, as combined with the inspection of the container base with regard to dirt, bubbles, inclusions, holes, crystalline areas, and eccentricity of the injection point within the stretch-blow-molding machine in a common camera station.

11. A method according to claim 1, wherein the at least one camera is spatially-resolving electronic camera.

12. A method according to claim 1, whereby the directed light is generated by an optical unit comprising at least one of a stop, a directing foil, a lens system or one or more other optical units.

13. A method according to claim 1, further comprising generating the directed light by an optical unit comprising at least one of a stop, a directing foil, a lens system or one or more other optical units, and whereby the directed light at the wedge angle does not arrive at the camera.

14. A method for controlling the quality of a stretch-blow-molded plastic container (9), the method comprising optically inspecting a container base (12) of the plastic container, making visible one or both of (a) characteristic structures of the container base and (b) distribution of material (18, 19, 20) at the container base (12) of the plastic container (9) by illumination means, recording the characteristic structures and distribution of material with at least one camera, deriving quality features therefrom by image processing algorithms, and making visible one or both of the characteristic structures and the distribution of material through a recognition of a wedge angle between inner and outer surfaces of the container with the aid of directed light, further comprising generating the directed light by an optical unit comprising at least one of a stop, a directing foil, a lens system or one or more other optical units, and whereby the directed light at the wedge angle does not arrive at the camera.

15. A method according to claim 14, and via the illumination means illuminating the container base, and via the electronic camera viewing the base through the container mouth opening in a transmitted light process.

16. A method according to claim 14, and comparing individual quality features or a combination of such features with predefined limits, and, if the limit values are exceeded, removing the containers objected to.

17. A method according to claim 14, and statistically associating the determined quality features and the derived magnitudes, respectively, with the respective multiply provided production tools in the stretch-blow-molding machine.

18. A method according to claim 14, further comprising controlling the parameters of the stretch-blow-molding process in response to at least one of the desired quality features.

19. A method according to claim 14, as combined with the inspection of the container base with regard to dirt, bubbles, inclusions, holes, crystalline areas, and eccentricity of the injection point within the stretch-blow-molding machine in a common camera station.

20. A method according to claim 14, wherein the at least one camera is spatially-resolving electronic camera.

* * * * *